United States Patent [19]

Farzin-Nia

[11] Patent Number: 5,281,133
[45] Date of Patent: Jan. 25, 1994

[54] RAPID PALATAL EXPANSION DEVICE

[75] Inventor: Farrokh Farzin-Nia, Inglewood, Calif.

[73] Assignee: Ormco Corporation, Glendora, Calif.

[21] Appl. No.: 976,519

[22] Filed: Nov. 16, 1992

[51] Int. Cl.5 .............................................. A61C 3/00
[52] U.S. Cl. ...................................................... 433/7
[58] Field of Search ........................................... 433/7

[56] References Cited

U.S. PATENT DOCUMENTS

| 2,927,578 | 3/1960 | Gerbrands | 433/7 |
| 3,832,778 | 9/1974 | Wallshein | 433/7 |
| 3,835,540 | 9/1974 | Biederman | 433/7 |
| 4,347,054 | 8/1982 | Kraus et al. | 433/7 |
| 4,379,693 | 4/1983 | Wallshein | 433/7 |
| 4,571,178 | 2/1986 | Rosenberg | 433/7 |
| 4,713,000 | 12/1987 | Rosenberg | 433/7 |
| 5,007,828 | 4/1991 | Rosenberg | 433/7 |

FOREIGN PATENT DOCUMENTS 998076 1/1952 France .
1150055 1/1958 France ................................. 433/7

Primary Examiner—John J. Wilson
Attorney, Agent, or Firm—Wood, Herron & Evans

[57] ABSTRACT

An orthodontic rapid palatal expansion (RPE) device is disclosed which includes dual body members and four guide rods for increased stability and an increased range of palatal expansion. A jack screw threadably engages each body member and, upon rotation, generates an expansive force which is applied to the palate via the guide rods. A jack screw actuating head with multiple actuating apertures provides the means for rotating the jack screw, and a locking mechanism is included for the dual purposes of (1) preventing unwanted negative rotation or unwinding of the jack screw and (2) providing sensible indications of the positive rotation of the jack screw. Each guide rod is attached to a tooth by means of an attachment sleeve which allows for removal and replacement of the RPE device without removing molar bands secured to the teeth.

14 Claims, 1 Drawing Sheet

RAPID PALATAL EXPANSION DEVICE

FIELD OF THE INVENTION

This invention relates to orthodontic devices, and more particularly to palatal expansion devices.

BACKGROUND OF THE INVENTION

A frequently encountered problem in orthodontic patients is that the arch width or palate is too narrow. This may result in a deformed and/or elongated arch and crowding of the teeth, which in turn can lead to other medical and dental problems. Devices are available which are intended to overcome these problems. Such devices, known as rapid palatal expansion (RPE) devices, comprise a rigid apparatus that includes a screw mechanism which is rotatable to apply an expansive force to the patient's palate. Over time, the expansive forces delivered by RPE devices results in widening of the palate.

Utilizing known devices, palatal expansion is accomplished by periodically (once or twice daily) turning a jack screw incorporated into the expansion device structure. One shortcoming of known RPE devices is that their palatal expansion capability is limited by the length of the screw and/or the associated structure which transfers the expansive force from the screw to the palate. Furthermore, these devices tend to become structurally unstable as they reach their limits of expansion. Currently available palatal expansion devices may provide up to approximately 11 mm of expansion. Oftentimes, however, the range of palatal expansion required in treating a patient is greater than that which is available from a single device. For example, the initial treatment of a patient with a very narrow palate may require a narrow and compact expansion device. As the patient's treatment progresses and the palatal width increases, the initial expansion device becomes inadequate. As a result, the orthodontist must disconnect the device from the patient's teeth, remove it and replace it with a device having a larger palatal expansion range for continued treatment. This drawback requires the clinician and the patient to devote more chair time during the course of the orthodontic treatment, which adds to the overall expense of the process.

Another drawback associated with known palatal expansion devices is the inability to accurately determine how much rotation of the jack screw is required or has been accomplished. An additional and related drawback is that the jack screw may have a tendency to "unwind," resulting in contraction of the device, a decrease in the force applied to the patient's teeth and palate, and unwanted sagittal movement of the teeth and palate.

Therefore, a need exists for an improved rapid palatal expansion device which overcomes the drawbacks associated with existing palatal expansion devices.

SUMMARY OF THE INVENTION

In accordance with the present invention, an improved rapid palatal expansion device is disclosed.

The rapid palatal expansion (RPE) device of the present invention consists of two opposed body members, preferably substantially identical in design, each threadably engaged by a jack screw disposed therebetween for providing an expansive force to a patient's palate. Each body member includes two guide rods which are brazed, welded, or otherwise affixed thereto, two through holes for slidably receiving the respective guide rods of the opposite body member, and one threaded bore for receiving and engaging the jack screw mechanism. Additionally, the jack screw includes an actuating head having a plurality, preferably six, circumferentially spaced actuating apertures by means of which the jack screw is rotated to provide the desired expansive force.

Once assembled, the respective guide rods of each body member function both as guides for stabilizing the device as it is incrementally expanded, and as supports for attaching the device to molar bands in place on a patient's teeth. The expansive force generated by positive rotation of the jack screw actuating head is transmitted to the patient's palate via the guide rods. Since the RPE device of the present invention has four guide rods, it offers more stability and structural integrity than the known palatal expansion devices. This is especially important and significant due to the greater expansion distances which may be achieved using the RPE device of the present invention.

The attachment mechanism for attaching the device of the present invention to a patient's teeth includes a plurality of sleeves, each of which receives the distal end of a respective guide rod. The sleeves also each receive a tooth band post which is brazed or welded in a vertical orientation to a molar tooth band attached to the patient's tooth. The sleeve includes a pair of set screws to selectively engage and retain both the guide rod and tooth band post during attachment and use of the RPE device. One of the sleeve set screws frictionally engages the tooth band post and the other engages the guide rod to permit easy attachment and removal of the RPE device without having to remove the molar bands in place in the patient's mouth. In this way, an RPE device of the present invention can be mounted to bands in a patient's mouth and subsequently removed by releasing the set screws which engage the guide rods. Thereafter, another RPE device may be substituted and attached to the existing sleeves and molar bands in place in the patient's mouth. One benefit of this type of attachment mechanism is that the entire course of a single patient's palatal treatment, which may encompass a series of two or more expansion devices, may be accomplished while employing the same molar band attachment initially installed on the patient's teeth.

In use, the RPE device of the present invention is expanded outwardly along the axis of the jack screw in response to positive incremental rotation of the jack screw actuating head. This positive rotation is accomplished utilizing a key which is inserted into one of the actuating apertures. To prevent unwinding of the jack screw, which may result in unwanted sagittal movement of the palate, the RPE device is provided with a locking mechanism. The locking mechanism comprises a strap with a pair of curled ends for attaching the strap to a pair of guide rods associated with one of the body members such that the strap lock mechanism covers the jack screw actuating head. The strap includes a nipple-like projection which is designed to resiliently engage an aperture in the jack screw actuating head and thereby prevent undesired negative rotation of the jack screw. The nipple-like projection sequentially engages each aperture in the actuating head as the head is rotated. In addition to preventing unwanted rotation of the jack screw, the locking mechanism provides a sensible indication when the actuating head is being rotated and indicates the amount of incremental rotation. Both an audible and vibrational indication is produced as the actuating head is rotated and the nipple-like projection successively engages each aperture in the actuating head. In this way, the operator of the RPE device can accurately and incrementally control the expansive force delivered by the device.

These and other objectives and features of the invention will become more fully apparent from the following detailed description taken in conjunction with the accompanying drawings.

DETAILED DESCRIPTION OF THE INVENTION

Figure 1:
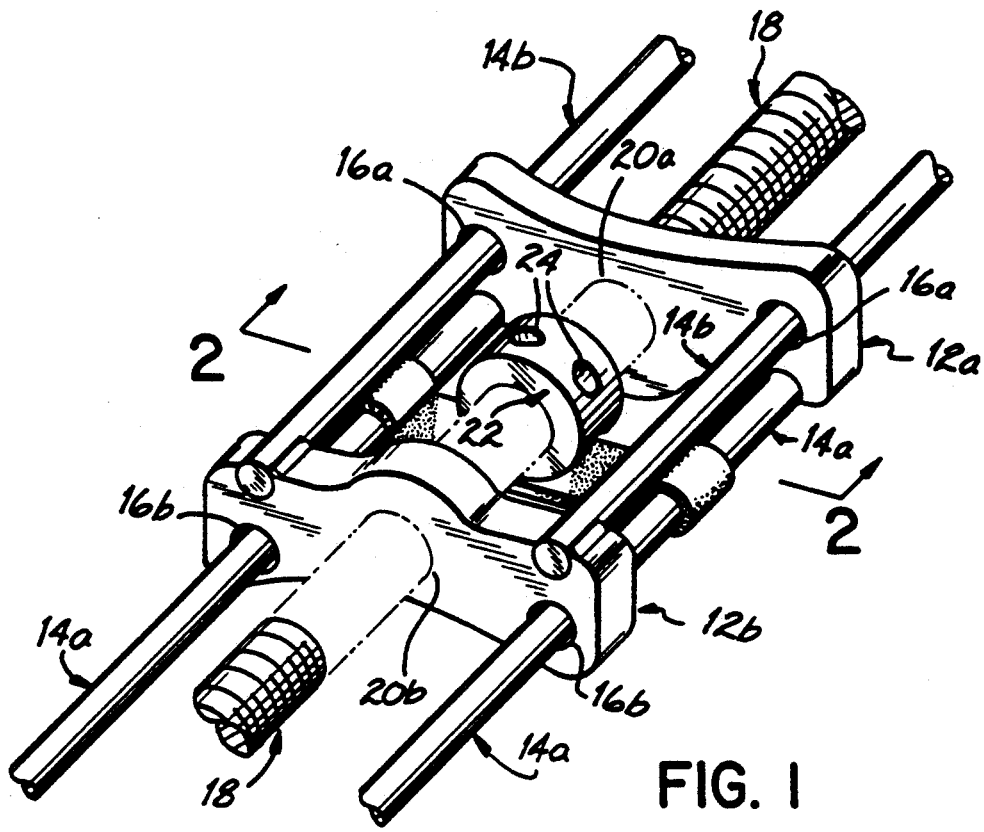
FIG. 1 is a perspective view, partially broken away, of an RPE device of the present invention.

A rapid palatal expansion device 10 according to the present invention has two opposed main body members 12a and 12b as shown in FIG. 1. Body members 12a and b are substantially identical and each has a pair of spaced, parallel guide rods 14a and 14b, respectively, brazed or welded thereto. In addition, body members 12a and 12b each have a pair of through holes 16a and 16b, respectively, for slidably receiving the guide rods 14a and 14b of the opposed body member. Preferably, each body member 12a, 12b is generally yoke shaped and the respective guide rods 14a or 14b extend from the associated body member in the same direction and are generally parallel. Through holes 16a, 16b are positioned adjacent guide rods 14a, 14b on each yoke shaped body member 12a, 12b. With this configuration, RPE device 10 is assembled by inverting one body member relative to the opposed body member such that guide rods 14a of body member 12a are slidably received in through holes 16b of the opposed body member 12b. Likewise, guide rods 14b of body member 12b are slidably received in through holes 16a of opposed body member 12a. This arrangement of four guide rods results in increased stability and structural integrity of RPE device 10 and allows for a wider palatal expansion with a single device than was heretofore possible. Expansion lengths as great as 20 mm can be achieved with RPE device 10.

A jack screw 18 engages each body member 12a, 12b through a threaded bore 20a, 20b in the central region of each body member. The end sections of jack screw 18 are threaded in a reverse orientation from one another and are designed to mesh with a respective bore 20a, 20b in body member 12a, 12b, in a manner well known in the art. The central section of jack screw 18 consists of jack screw actuating head 22. Jack screw actuating head 22 is generally cylindrical, oriented coaxially with jack screw 18, and has a plurality of actuating apertures 24 circumferentially spaced around its surface. In the preferred embodiment shown, actuating head 22 has six equally spaced circumferential apertures 24, spaced 60° apart.

In operation, a key (not shown) is inserted into an aperture 24 of actuating head 22 and rotated through an arc about jack screw 18, thereby rotating jack screw 18. The oppositely threaded configuration of the ends of jack screw 18 causes body members 12a and 12b to be brought closer together or spread farther apart depending on the direction of rotation of the jack screw. For example, positive rotation of jack screw actuating head 22 causes opposed body members 12a and 12b to be drawn closer together, thereby effectively extending the separation distance between distal ends 26 of guide rods 14a, 14b and imparting an expansive, outwardly directed force. Similarly, negative rotation of actuating head 22 results in contraction of the distance between distal ends 26 of guide rods 14a, 14b. Distal ends 26 are the ends of guide rods 14a, 14b which are distant from the body members 12a, 12b.

Figure 2:
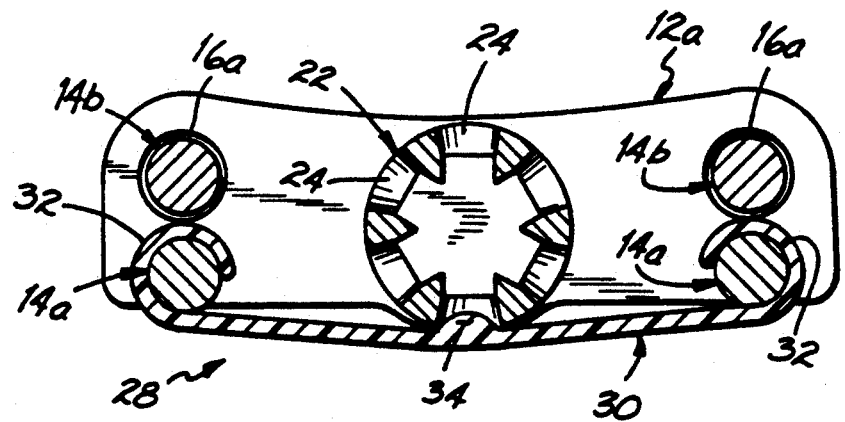
FIG. 2 is a cross-sectional view taken along line 2—2 of FIG. 1.

A locking mechanism 28 is provided for RPE device 10. As shown in FIG. 2, locking mechanism 28 consists of a strap 30 having a pair of opposed curled ends 32 which attach the strap to one of the pairs of guide rods 14a or 14b extending from one of the body members 12a and 12b. Each curled end 32 of strap 30 clamps around and grips a respective guide rod. Strap 30 has a nipple-like projection 34 centrally located therein. In a preferred embodiment, projection 34 is integrally formed in strap 30. Strap 30 is positioned on guide rods 14 such that it covers jack screw actuating head 22 and projection 34 is received in one of the actuating head apertures 24. Projection 34 resiliently but firmly engages aperture 24, thereby preventing unwanted negative rotation of actuating head 22 and jack screw 18, which may result in sagittal displacement of the rapid palatal expansion device 10 and the patient's palate.

When a key is inserted into an exposed aperture 24 and actuating head 22 is rotated, the projection 34 is displaced from its resident aperture 24 due to flexing of strap 30 and frictionally translates along the circumferential surface of actuating head 22 until the next successive aperture 24 is positioned to receive projection 34. At this point, the operator of RPE device 10 senses a vibrational and audible indication that projection 34 has engaged and is again seated in an aperture 24, thereby positively indicating incremental rotation of the jack screw. Utilizing a locking mechanism 28 as described allows the operator of the RPE device 10 to accurately determine the amount of rotation and the attendant expansive force applied to the palate, as prescribed by the clinician. In addition, jack screw 18 remains secure from unwanted negative rotation, resulting in undesirable sagittal displacement of the device and the palate.

Figure 3:
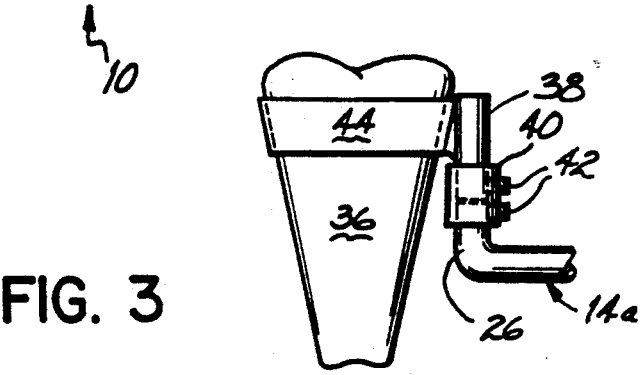
FIG. 3 is a side elevation, partially broken away, of an RPE device mounted to a tooth.

In a preferred embodiment, and as shown in FIG. 3, RPE device 10 includes means to affix the device to a patient's teeth such that the expansive force generated by rotation of the jack screw 18 is transmitted to the teeth and/or palate. Distal end 26 of each guide rod is formable to provide for convenient and adaptable attachment to the dental structure in a patient's mouth. In addition, formable distal ends 26 of the guide rods allow RPE device 10 to be positioned in the gingival or arch areas of the patient's mouth to avoid lingual interference.

As shown, the distal end 26 of guide rod 14a is secured in endwise, abutting relationship with a tooth band post 38 by means of a sleeve 40. Distal end 26 and tooth band post 38 are respectively inserted through opposite ends of a cylindrical bore in sleeve 40 and are frictionally secured therein by a pair of set screws 42; one set screw 42 engages distal end 26, and the other set screw 42 engages tooth band post 38. Thus, post 38 and distal end 26 can be selectively joined or separated using sleeve 40, and rotation of an individual set screw 42 thereby secures or releases the respective rod. An opposite end of post 38 not secured in sleeve 40 is preferably attached to a molar tooth ban 44 which is secured around the circumference of a patient's tooth 36. In this manner, expansive movement of guide rod 14 of RPE device 10 transmits an expansive force through post 38 to molar band 44, resulting in the desired displacement of the patient's tooth and palate. In a preferred embodiment, post 38 is brazed or welded to the molar band 44 in a vertical orientation as shown, thereby minimizing lingual interference. Although not specifically shown, it will be appreciated that each of the four guide rods 14a, 14b has a distal end 26 which is affixed to a tooth in the above-described manner such that the expansive forces generated by RPE device 10 are transferred to the patient's palate via the two pairs of guide rods 14a, 14b on opposite sides of the dental arch.

It will also be appreciated that as an alternative to using a sleeve 40 which includes set screws 42 to engage post 38 and distal end 26, sleeve 40 itself may be internally threaded (not shown) to engage a post 38 which has a threaded end and to engage a threaded distal end of each guide rod. Additionally, although not shown explicitly, sleeve 40 may include one set screw and also be internally threaded to engage either a threaded band post 38 or a threaded distal end 26 of a guide rod. Moreover, sleeve 40 may be of any desired configuration, such as oval or hexagonal, and is not limited to being cylindrical, as is shown.

The capability of selectively engaging and disengaging individual tooth band posts 38 and distal ends 26 from sleeves 40 is advantageous since it permits the clinician to readily replace one RPE device with another without removing and replacing molar bands 44. This permits greater flexibility during patient treatment.

From the above description of the present invention, including a preferred embodiment thereof, various changes and modifications will become apparent to persons skilled in the art. Therefore, the scope of the present invention is not to be limited to the specific embodiments and examples provided herein, but is to be accorded a scope commensurate with the appended claims.

What is claimed is:

1. A rapid palatal expansion device comprising:
   first and second opposed body members, each said body member having a pair of spaced parallel guide rods extending therefrom and a pair of through holes for slidably receiving said guide rods of said opposed body member, each said guide rod including attachment means at a distal end thereof for affixing said guide rod to a tooth;
   force-applying means for expanding said device to apply an expansive force to the palate via said guide rods while causing said first and second body members to be drawn toward one another; and
   locking means for incrementally engaging said force-applying means to prevent unwanted contraction of said device.

2. A rapid palatal expansion device according to claim 1 wherein said locking means comprises:
   a strap having a pair of opposed ends which are respectively attached to said guide rods of one of said pairs of guide rods; and
   a nipple-like projection for resiliently engaging said force-applying means, said projection being centrally located on said strap.

3. A rapid palatal expansion device according to claim 2 wherein said force-applying means comprises:
   a jack screw including an actuating head having a plurality of circumferentially spaced actuating apertures, said jack screw threadably engaging a bore in each said body member, said locking strap positioned with respect to said actuating head such that said projection resiliently and sequentially engages each said actuating aperture as said actuating head is rotated.

4. A rapid palatal expansion device according to claim 2 wherein said projection is integrally formed in said locking strap.

5. A rapid palatal expansion device according to claim 1 wherein said force-applying means is
   a jack screw including an actuating head having a plurality of circumferentially spaced actuating apertures, said jack screw threadably engaging a bore in each said body member.

6. A rapid palatal expansion device according to claim 5 wherein said actuating head has six equally spaced actuating apertures.

7. A rapid palatal expansion device according to claim 1 wherein said guide rod attachment means comprises:
   a tooth band capable of being fixedly secured around a tooth;
   a tooth band post fixedly attached to said tooth band; and
   a sleeve for detachably joining said tooth band post to said distal end of a guide rod, said sleeve having a pair of set screws for frictionally engaging said guide rod and said tooth band post when inserted therein.

8. A rapid palatal expansion device according to claim 7 wherein said tooth band post is vertically attached to said band to avoid lingual interference.

9. A rapid palatal expansion device according to claim 1 wherein each said guide rod is formable to mate with said attachment means and to avoid lingual interference.

10. A rapid palatal expansion device comprising:
    first and second opposed body members, each said body member having a pair of spaced parallel guide rods extending therefrom and a pair of through holes for slidably receiving said guide rods of said opposed body member:
    a jack screw including an actuating head having six actuating apertures spaced equally about the circumference of said actuating head, said jack screw threadably engaging a bore in each said body member to expand said device and apply an expansive force to the palate via said guide rods as said actuating head is rotated;
    a locking strap having a pair of opposed ends which are respectively attached to said guide rods of one of said pairs of guide rods, said strap having a nipple-like projection centrally located and integrally formed therein for resiliently and sequentially engaging each said aperture as said actuating head is rotated.

11. A rapid palatal expansion device of claim 10 further comprising:
    a tooth band capable of being fixedly secured around a tooth;
    a tooth band post fixedly attached to said tooth band; and
    a sleeve for detachably joining said tooth band post to said distal end of a guide rod, said sleeve having a pair of set screws for frictionally engaging said guide rod and said tooth band post when inserted therein.

12. A rapid palatal expansion device of claim 11 wherein each said guide rod is formable to mate with said sleeve and to avoid lingual interference.

13. A locking device for use in combination with a rapid palatal expansion device having at least one pair of guide rods and a jack screw, comprising:

a strap having a pair of opposed ends which are configured to be respectively attachable to the guide rods of the rapid palatal expansion device; and a nipple-like projection for resiliently engaging the jack screw of the rapid palatal expansion device, said projection being centrally located on said strap.

14. A locking device according to claim 13 wherein said projection is integrally formed in said strap.

* * * * *